(12) United States Patent
Bartholomew

(10) Patent No.: US 7,503,908 B2
(45) Date of Patent: Mar. 17, 2009

(54) NEEDLELESS ACCESS PORT VALVES

(75) Inventor: Joel Bartholomew, Danielsvile, PA (US)

(73) Assignee: B. Braun Medical Inc., Bethlehem, PA (US)

(*) Notice: Subject to any disclaimer, the term of this patent is extended or adjusted under 35 U.S.C. 154(b) by 550 days.

(21) Appl. No.: 11/188,192

(22) Filed: Jul. 22, 2005

(65) Prior Publication Data

US 2007/0038189 A1  Feb. 15, 2007

(51) Int. Cl.
*A61M 5/00* (2006.01)
(52) U.S. Cl. .................... 604/249; 604/246
(58) Field of Classification Search ............ 604/246, 604/247, 249, 537
See application file for complete search history.

(56) References Cited

U.S. PATENT DOCUMENTS

| | | | | |
|---|---|---|---|---|
| 4,683,916 A | * | 8/1987 | Raines | 137/854 |
| 5,269,771 A | * | 12/1993 | Thomas et al. | 604/539 |
| 5,441,487 A | * | 8/1995 | Vedder | 604/167.03 |
| 5,509,912 A | | 4/1996 | Vaillancourt et al. | |
| 5,514,116 A | | 5/1996 | Vaillancourt et al. | |
| 5,669,891 A | | 9/1997 | Vaillancourt | |
| 5,700,248 A | * | 12/1997 | Lopez | 604/249 |
| 5,776,113 A | | 7/1998 | Daugherty et al. | |
| 5,950,986 A | | 9/1999 | Daugherty et al. | |
| 6,063,062 A | * | 5/2000 | Paradis | 604/249 |
| 6,364,869 B1 | * | 4/2002 | Bonaldo | 604/537 |
| 6,585,229 B2 | * | 7/2003 | Cote et al. | 251/149.1 |
| 6,595,981 B2 | | 7/2003 | Huet | |
| 6,869,426 B2 | | 3/2005 | Ganem | |
| 7,014,169 B2 | * | 3/2006 | Newton et al. | 251/149.6 |
| 2002/0133124 A1 | * | 9/2002 | Leinsing et al. | 604/256 |
| 2002/0147431 A1 | * | 10/2002 | Lopez et al. | 604/256 |
| 2003/0208165 A1 | * | 11/2003 | Christensen et al. | 604/256 |
| 2006/0264841 A1 | * | 11/2006 | Cote et al. | 604/247 |
| 2007/0038189 A1 | * | 2/2007 | Bartholomew | 604/249 |

* cited by examiner

*Primary Examiner*—Nicholas D Lucchesi
*Assistant Examiner*—Aarti Bhatia
(74) *Attorney, Agent, or Firm*—Klein, O'Neill & Singh, LLP

(57) ABSTRACT

Needleless access port valves are generally discussed herein with particular discussions on needleless access port valves incorporating a moving cannula. The moving cannula may be part of a valve core having a diaphragm, a septum, and a plurality of biasing members. A plurality of openings disposed on the hollow cannula permit fluid flow between the inlet and the outlet of the valve housing. The inlet and the outlet may be placed in fluid communication by inserting a medical implement in the inlet and moving the valve core.

22 Claims, 2 Drawing Sheets

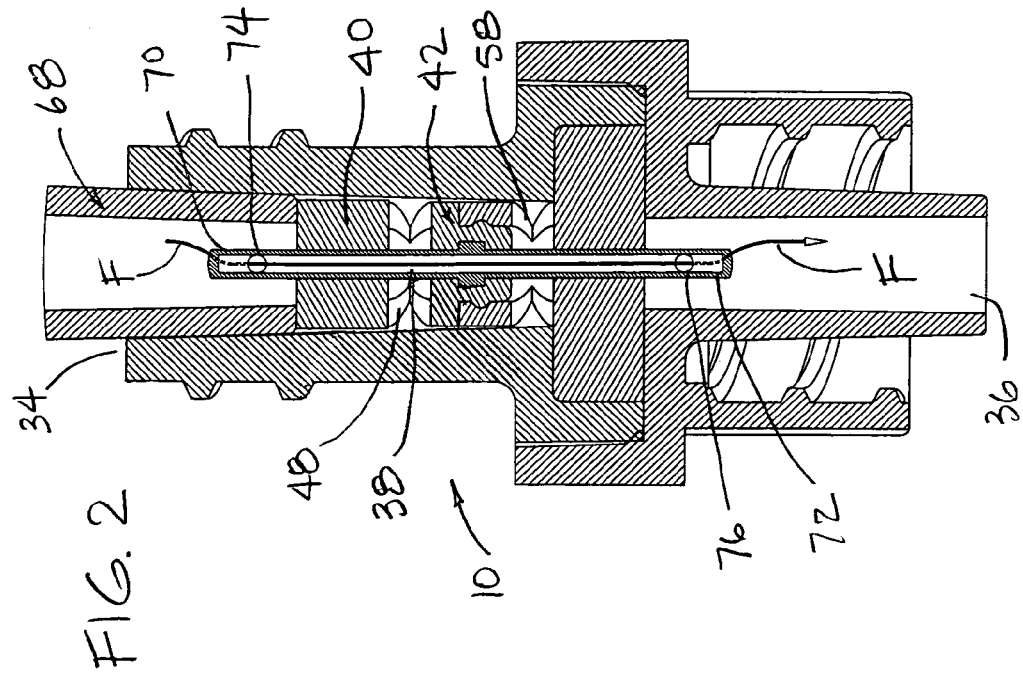
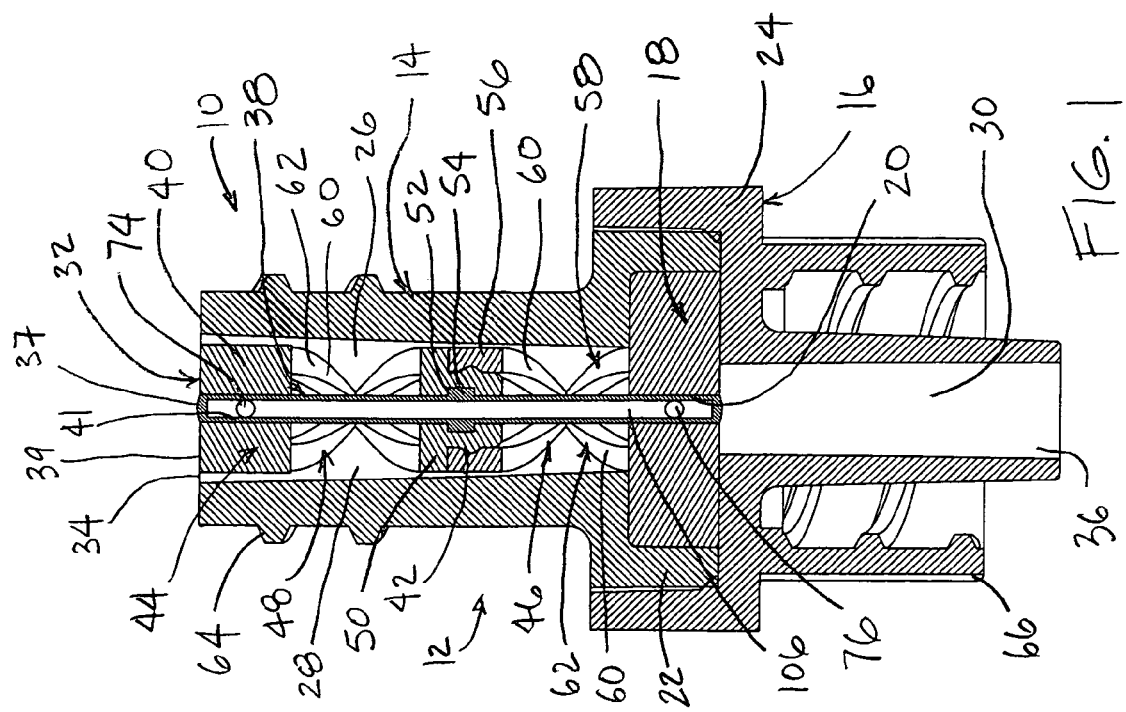

NEEDLELESS ACCESS PORT VALVES

Needleless access port valves are generally discussed herein with particular discussions on needleless access port valves comprising a moving cannula.

BACKGROUND

Needleless access port valves are widely used in the medical industry for accessing an IV line and/or the internals of a patient or subject. Generally speaking, prior art valves utilize a valve housing in combination with a movable internal plug or piston to control the flow of fluid through a valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a valve for controlling fluid flow comprising a valve housing and a valve core disposed therein; the valve housing comprising an inlet and an outlet; the valve core comprising a cannula comprising a first end and a second end, an engagement collar comprising a first side and a second side positioned between the first end and the second end of the cannula; a first biasing member comprising a first end and a second end, the second end of the first biasing member positioned proximate the first side of the engagement collar and the first end of the first biasing member positioned proximate a diaphragm located closer to the inlet than the outlet of the housing; a second biasing member comprising a first end and a second end, the second end of the second biasing member positioned proximate a septum located closer to the outlet than the inlet of the housing and the first end of the second biasing member positioned proximate the second side of the engagement collar; and wherein the cannula comprises a first opening near the first end and a second opening near the second end.

The present invention may also be practiced by providing a valve for controlling fluid flow comprising a valve housing and a valve core disposed therein; the valve housing comprising an inlet, an outlet, and an interior cavity; the valve core comprising a cannula comprising a hollow core, a plurality of openings, and an engagement collar; a diaphragm and a septum each comprising an opening and having the cannula passing therethrough positioned in the interior cavity of the housing; a first biasing member biased against the diaphragm and the engagement collar; and a second biasing member biased against the engagement collar and the septum.

In yet another aspect of the present invention, there is provided a valve for controlling fluid flow comprising a housing comprising an upper housing chamber attached to a lower housing chamber; a valve core comprising a first plunger means aligned in series with a second plunger means for serially compressing and expanding to move the valve core from an open position to a closed position; and wherein the cannula comprises a plurality of openings.

In yet another aspect of the present invention, there is provided a biasing member made from a thermoplastic elastomer material for biasing the valve core.

In still yet another aspect of the present invention, there is provided two coil springs for biasing the valve core.

Other aspects and variations of the valve assemblies summarized above are also contemplated and will be more fully understood when considered with respect to the following disclosure.

BRIEF DESCRIPTION OF THE DRAWINGS

These and other features and advantages of the present invention will become appreciated as the same become better understood with reference to the specification, claims and appended drawings wherein:

FIG. 1 is a semi-schematic cross-sectional side view of a needleless access port valve provided in accordance with aspects of the present invention, which shows the valve in a closed position and having two biasing members for biasing a valve core;

FIG. 2 is a semi-schematic cross-sectional side view of the valve of FIG. 1 in a used position, which shows the valve core urged by a medical implement into a compressed second position;

DETAILED DESCRIPTION

Figure 4:
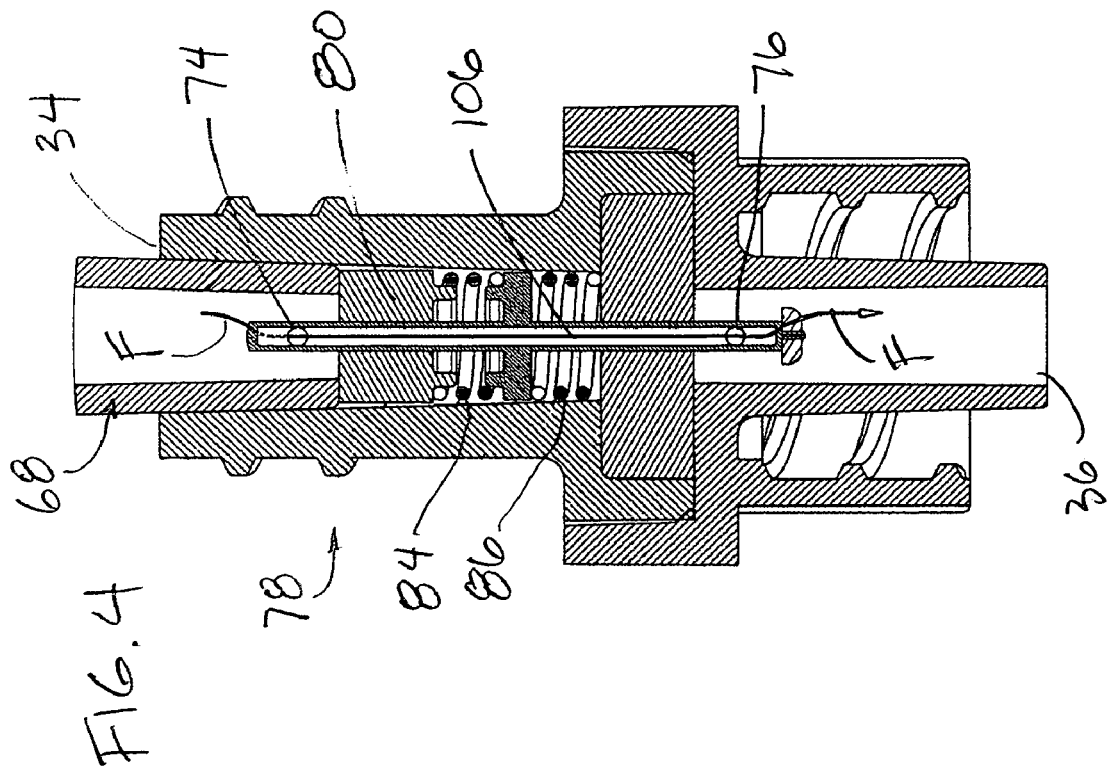
FIG. 4 is a semi-schematic cross-sectional side view of the valve of FIG. 3 in a used position.

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Turning now to FIG. 1, a semi-schematic cross-sectional side view of a needleless access port valve provided in accordance with aspects of the present invention is shown, which is generally designated 10. In one aspect of the present invention, the valve 10 comprises a multi-component housing 12 comprising an upper housing component 14 secured to a lower housing component 16. A compressible septum 18 comprising a bore 20 is compressed between a cavity defined by the collar 22 of the upper housing component 14 and the collar 24 of the lower housing component 16. The compressible septum 18 functions as a seal to seal the interior surfaces compressed there-against by the two collars 22, 24. In one exemplary embodiment, the two housing components 14, 16 are made from a hard thermoplastic material, which may include, for example, polycarbonate, ABS, or acrylic, just to name a few. In an alternative embodiment, ribs may be added in the cavity defined by the two collars to provide greater compression against the septum.

The upper and lower housing components 12, 14 define an interior cavity 26 for passing fluid therethrough, which comprises an upper interior cavity section 28 and a lower interior cavity section separated from one another by the septum 18. A valve core 32 comprising a first end and a second end is disposed in the interior cavity 26 of the housing for controlling fluid flow between the valve inlet 34 and the valve outlet 36. In one exemplary embodiment, the valve core 32 comprises a cannula 38, a diaphragm 40, and an engagement collar 42 comprising a first side facing the inlet and a second side facing the outlet. The diaphragm 40, the engagement collar 42, and the bore 20 of the septum 18 interact with the cannula 38 when an external force is exerted on the valve core 32 to open fluid communication between the inlet 34 and the outlet 36, as further discussed below. The bore 20 and the cannula 38 preferably engage one another with about a 1 mil to about a 3 mil total interference fit. The cannula 38 is preferably hollow, has two sealed ends, and incorporates an opening proximate each of the sealed ends, as further discussed below. The cannula 38 may be made from a hard thermoplastic material, which may include, for example, polycarbonate, ABS, or acrylic, just to name a few. Alternatively, the cannula may be made from metal, which may include, for example, stainless steel or nitinol.

In one exemplary embodiment, the valve core 32 comprises an upper plunger 44 and a lower plunger 46, which are aligned in series. The upper plunger 44 comprises the upper diaphragm 40, a biasing element 48 comprising a first end and a second end, and a lock piston 50, which forms part of the engagement collar 42. In one aspect of the present invention, the lock piston 50 incorporates an internal female detent 52 for mating engagement with a male detent 54 formed on the cannula 38. The mating engagement between the female detent 52 and male detent 54 fixes the lock piston 50 to the cannula 38 so that the lock piston and the cannula move in unison when a force is exerted on the valve core 32 to move the valve core. In a preferred embodiment, the diaphragm 40, the biasing element 48, and the lock piston 50 are integrally formed from a thermoplastic elastomer material (TPE). Exemplary TPE materials that may be used to form the upper plunger include Santoprene and Kraton. In another embodiment, the TPE is a member of the copolyamide (COPA) family of thermoplastic elastomers. In a preferred embodiment, the COPA is copolyamide thermoplastic elastomer having a commercial trade name PEBAX®. However, other TPEs may also be used to make the diaphragm 40, the biasing element 48, and the lock piston 50, including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics. In yet another embodiment, silicone or rubber (polyisoprene) may be used to make the diaphragm 40, the biasing element 48, and the lock piston 50.

Alternatively, only the diaphragm 40 and the biasing element 48 are integrally formed. Still alternatively, only the biasing element 48 and the lock piston 50 are integrally formed. Yet still alternatively, the diaphragm 40, the biasing element 48, and the lock piston 50 are separately formed components. The diaphragm 40 is preferably formed with a bore 41 for receiving the cannula 38, which contact one another with a slight interference fit, of about 1 mil to about 3 mil total clearance. Preferably, the upper arcuate shaped end 37 of the cannula projects slightly above the top surface 39 of the diaphragm 40 when the valve is in the closed position as shown, although not required for functionality. This relative orientation minimizes the possibility of cutting or scouring the interior surface of the bore 41 by the end of the cannula 38 when the two components move relative to one another.

In one exemplary embodiment, the lower plunger 46 comprises a lock sleeve 56 and a biasing element 58 comprising a first end and a second end. The lock sleeve 56 cooperates with the lock piston 50 on the upper plunger 44 to form the engagement collar 42. In a preferred embodiment, the engagement between the lock sleeve 56 and the lock piston 50 comprises a detent engagement. However, a more permanent engagement, such as adhesive or heat welding (from a heat source or from a laser), may be used to secure one to the other. In one exemplary embodiment, the lock sleeve 56, the biasing element 58, and the septum 18 are integrally formed. Alternatively, only the lock sleeve 56 and the biasing element 58 are integrally formed. Still alternatively, only the biasing element 58 and the septum 18 are integrally formed. Yet still alternatively, the lock sleeve 56 may be eliminated and the biasing element 58 directly abutting the lock piston 50.

In one exemplary embodiment, the two biasing elements 48, 58 each comprises an eight-legged 60 structure with four of the eight legs 60 intersecting one another to form two each four-legged biasing structures 62. In the cross-sectional view of FIG. 1, only one four-legged biasing structure 62 is shown for the lower biasing element 58 and one for the upper biasing element 48. For each biasing element 48 and 58, a gap is provided between the two four-legged biasing structures 62 for passing the cannula 38 therebetween. Alternatively, a plurality of generally linear biasing elements may be incorporated instead of the four-legged biasing structures 62. The generally linear biasing elements each comprises two ends with each of the ends abutting the diaphragm 40, if incorporated as an upper biasing element, or abutting the septum 18, if incorporated as a lower biasing element, and the other end abutting the engagement collar 42. Each generally linear biasing element incorporates a pre-weakened spot for bending, collapsing, or flexing to accommodate movement when a force is applied on the valve core 32. The pre-weakened spot may be a kink, a cut-out, a neck, a notch, a softer material (i.e., a lower durometer), or their equivalents. Two, three, or four generally linear biasing elements may be incorporated for each biasing element unit. In yet another alternative embodiment, the biasing elements may embody helical shaped structure.

In one exemplary embodiment, the valve 10 may be assembled by first assembling the cannula 38 to the upper plunger 44. The lower plunger 46 is then mounted to the assembled parts by connecting the lock sleeve 56 to the lock piston 50 and passing the cannula 38 through the bore 20 of the septum 18. The valve core 32 is then inserted into the upper interior cavity 28 of the upper housing chamber 14 by way of the opening at the collar 22. The lower housing chamber 16 is then mounted to the assembled parts and sealed thereto. Although the valve 10 may be a luer slip type by incorporating a standard female luer at the inlet 34 and a standard male luer at the outlet 36, in a preferred embodiment, the inlet includes external threads 64 and the outlet 36 includes a threaded collar 66.

The valve 10 operates as a needleless injection site by connecting the outlet 36 to a first medical implement (not shown), such as an IV line and/or a catheter device. In the valve ready to use or closed position as shown in FIG. 1, fluid communication is terminated between the inlet 34 and the outlet 36 by the seal formed around the septum 18 and the interference fit between the cannula 38 and the bore 20 of the septum. A seal is not necessary although possible between the interior wall surface of the upper housing chamber 14, and respectively, the diaphragm 40 and the engagement collar 42.

When a second medical implement 68, such as a syringe, is inserted into the inlet 34, a distally directed force is exerted on the diaphragm 40. The distally directed force concurrently compresses the upper biasing element 48 and the lower biasing element 58 and moves the lock collar 42 distally. Because the lock collar 42 is fixed to the cannula 38, it moves the cannula 38 distally. As shown in FIG. 2, the two ends 70, 72 of the cannula 38 are exposed by the compression, which, if sufficiently compressed, also exposes the two openings 74, 76 on the cannula 38. The openings 74, 76 are preferably positioned on the side of the cannula, along the longitudinal length of the cannula, and are sealed by the bore 41 of the diaphragm 40 and the bore 20 of the septum 18 when the valve is in the first or closed position. In the valve second or used position shown, fluid communication is opened between the valve inlet 34 and the valve outlet 36 by way of the hollow cannula interior 106 and the two openings 74, 76. Fluid flow F from the first medical implement 68 to the second medical implement (not shown), or vice versa, may be carried out when the valve is in said second position.

Figure 3:
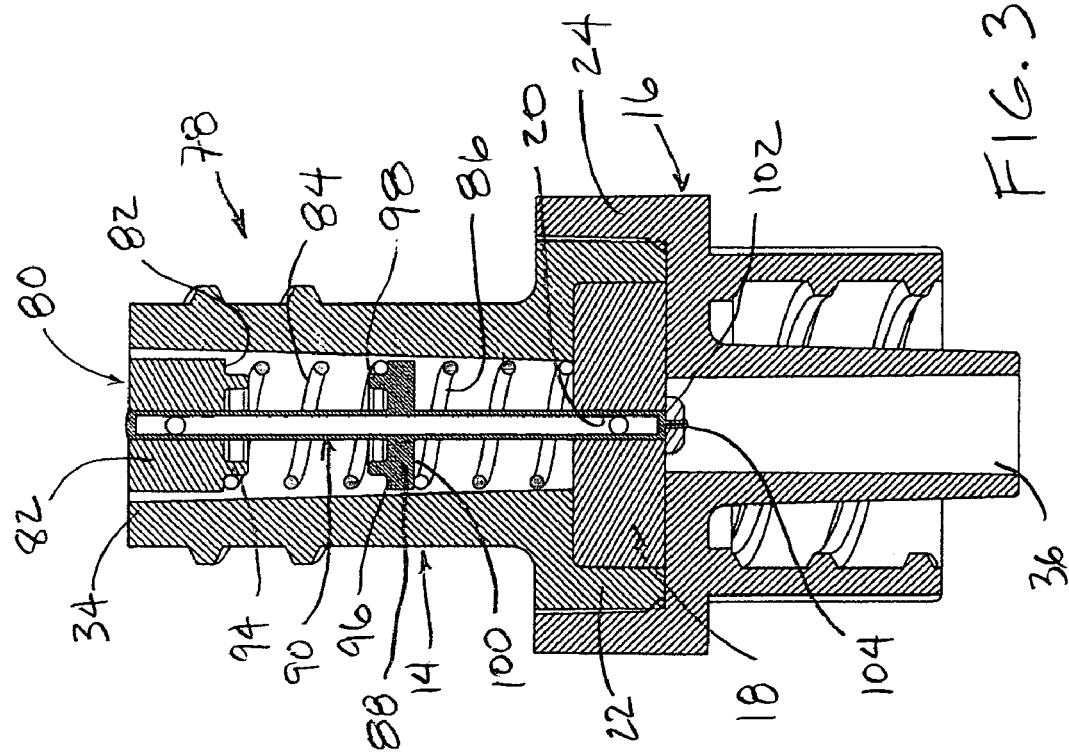
FIG. 3 is a semi-schematic cross-sectional side view of an alternative needleless access port valve provided in accordance with aspects of the present invention, which comprises two coiled springs.

The valve 10 returns to its first position from the second position when the second medical implement 68 is removed from the inlet 34. In essence, this removes the distally directed force from the valve core 32 and allows the two biasing members 48, 58 to return to a lesser flexed or biased state, which encompasses or includes a zero biased or flexed state FIG. 3 is an alternative valve 78 provided in accordance with aspects of the present invention. In the present alternative valve 78, the valve core 80 incorporates a modified diaphragm 82, biasing members 84, 86, engagement collar 88, and cannula 90. In one exemplary embodiment, a seat 92 is incorporated on the diaphragm 82 for abutting or contacting the upper biasing member 84, which in the alternative embodiment is a coil spring. A downwardly extending stem 94 is incorporated for locating the upper biasing member 84 relative to the diaphragm 82. The engagement collar 88 incorporates a similar seat 96 and upwardly extending stem 98 for abutting and locating the upper biasing member 84 relative to the engagement collar 88. A generally flat surface area 100 on an underside of the engagement collar 88 functions as a seat for the lower biasing member 86, which abuts the septum 18 at its other free end.

In one exemplary embodiment, the engagement collar 88 may be integrally formed to the cannula 90. Alternatively, the two may be separately formed and subsequently secured to one another using conventional secure means, such as heat welding, laser welding, or adhesive. A cap 102 is incorporated at the distal end of the cannula 90, which engages a tab 104 in a detent engagement. The cap 102 delimits the valve core 80 from dislodging proximally in the direction of the inlet 34 of the housing. The cap 102 may be made from the same material as the material used for making the cannula 90 or from a different material.

In one exemplary embodiment, the valve 78 may be assembled by first assembling the lower resilient member 86 onto the cannula 90 and then inserting the distal end of the cannula through the bore 20 of the septum 18. The cap 102 is then placed over the tab 104 to prevent the distal end of the cannula from dislodging proximally from the bore 20. Next, the upper resilient member 82 is placed over the cannula 90 followed by the diaphragm 82. The assembled valve core 80 is then inserted into the upper housing chamber 14 by way of the open distal end at the collar 22. Finally, the lower housing chamber 16 is abutted with the upper housing chamber 14 and the two fixedly secured to one another.

The alternative valve 78 may be used in the same manner as the valve described above with reference to FIGS. 1 and 2. Generally speaking, the valve 78 may be used by connecting the outlet 36 to a first medical implement (not shown), and inserting a second medical implement 68 through the inlet 34 to move the valve core 80 from a first or ready to use position shown in FIG. 3 to a second or used position shown in FIG. 4. This opens fluid communication between the inlet 34 and the outlet 36 by way of the two openings 74, 76 and the hollow core 106 of the cannula 90. Fluid F can then flow from the first medical implement 68 to the second medical implement as shown in FIG. 4, or vice versa.

The valve 78 may return to the first or ready to use position by removing the medical implement 68 from the inlet 34, which removes the downward force on the two biasing members 84, 86 thus allowing them to expand to their less compressed state, which includes or encompasses a zero compressed state.

Although limited embodiments of the needleless access valve assemblies and their components have been specifically described and illustrated herein, many modifications and variations will be apparent to those skilled in the art. For example, the various valves may incorporate luer-slips rather than luer threads, the engagement collar can attach to the cannula using different engagement means or alternatively co-molded to the cannula, color may be added to the housing for aesthetic appeal, more than one flow opening may be incorporated at each end of the cannula, etc. Furthermore, it is understood and contemplated that features specifically discussed for one valve embodiment may be adopted for inclusion with another valve embodiment, provided the functions are compatible. For example, the engagement collar may be separately attached to the cannula of the FIG. 3 valve embodiment rather than integrally formed. Accordingly, it is to be understood that the valve assemblies and their components constructed according to principles of this invention may be embodied other than as specifically described herein. The invention is also defined in the following claims.

What is claimed is:

1. A valve for controlling fluid flow comprising a valve housing and a valve core disposed therein;

the valve housing comprising an inlet, an outlet, and an interior cavity;

the valve core comprising a cannula comprising a hollow core, a plurality of openings, and an enlarged section between a proximal end and a distal end of the cannula mechanically engaged to an engagement collar;

a diaphragm located proximate the proximal end of the cannula and a septum located proximate the distal end of the cannula each comprising an opening and having the cannula passing therethrough, the diaphragm and the septum being positioned in the interior cavity of the housing;

a first biasing member biased against the diaphragm and the engagement collar;

a second biasing member biased against the engagement collar and the septum; and wherein the cannula is movable relative to the septum.

2. The valve as recited in claim 1, wherein the cannula projects through an upper surface of the diaphragm in both a closed position and a used position.

3. The valve as recited in claim 1, wherein the first biasing member and the second biasing member are both made from a metallic material.

4. The valve as recited in claim 1, wherein the plurality of openings comprises an inlet opening proximate a first end of the cannula and an outlet opening proximate a second end of the cannula.

5. The valve as recited in claim 1, wherein the first biasing member and the diaphragm are integrally formed to one another.

6. The valve as recited in claim 1, wherein the cannula comprises a first end and a second end and wherein a cap is mechanically coupled to the second end of the cannula.

7. The valve as recited in claim 1, wherein the engagement collar is integrally formed to the cannula.

8. The valve as recited in claim 1, wherein the septum is compressed between an upper housing chamber and a lower housing chamber.

9. The valve as recited in claim 1, further comprising exterior threads at the housing inlet.

10. The valve as recited in claim 1, further comprising a threaded collar at the housing outlet.

11. A valve for controlling fluid flow comprising:
a housing comprising an upper housing chamber attached to a lower housing chamber;
a valve core comprising a cannula and a first plunger aligned in series with a second plunger for serially compressing and expanding to move the valve core from an open position to a closed position; and
wherein the cannula comprises a proximal end near the tipper housing chamber and a distal end near the lower housing chamber and comprises a plurality of openings, the cannula being movable relative to the first plunger and the second plunger and the first and second plungers movable relative to one another.

12. The valve as recited in claim 11, wherein the cannula is engaged to an engagement collar.

13. The valve as recited in claim 11, wherein the cannula comprises a male detent for engaging an engagement collar.

14. The valve as recited in claim 11, wherein the first plunger comprises a biasing member, for biasing the valve core from an open position to a closed position, coupled to a diaphragm comprising a pre-formed passage.

15. The valve as recited in claim 14, wherein the second plunger comprises a biasing member for biasing the valve core from an open position to a closed position, coupled to a septum comprising a pre-formed passage.

16. The valve as recited in claim 15, wherein the two biasing members are mounted in series and are spaced apart from one another.

17. A valve for controlling fluid flow comprising:
a housing comprising an upper housing chamber comprising an inlet attached to a lower housing chamber comprising an outlet, the upper and lower housing chambers defining an interior cavity;
a valve core comprising an upper plunger located proximate the inlet, a septum spaced apart from the upper plunger located in the interior cavity of the housing, and a cannula passing through the upper plunger and the septum and having a mid section exposed to the interior cavity of the housing;
a biasing member for biasing the upper plunger away from the septum; and
wherein the cannula being movable relative to the upper plunger and the housing.

18. The valve as recited in claim 17, wherein the cannula is movable relative to the septum.

19. The valve as recited in claim 17, wherein the upper plunger is movable relative to the septum.

20. The valve as recited in claim 17, wherein the cannula comprises an opening sealed by the septum.

21. The valve as recited in claim 17, further comprising a second biasing member positioned serially relative to the biasing member.

22. The valve as recited in claim 21, further comprising an engagement collar positioned between the basing member and the second biasing member, said engagement collar being engaged to the cannula.

* * * * *

UNITED STATES PATENT AND TRADEMARK OFFICE
CERTIFICATE OF CORRECTION

PATENT NO. : 7,503,908 B2  Page 1 of 1
APPLICATION NO. : 11/188192
DATED : March 17, 2009
INVENTOR(S) : Joel Bartholomew It is certified that error appears in the above-identified patent and that said Letters Patent is hereby corrected as shown below:

In column 5, line 37, delete "state" and insert -- state. --, therefor.

In column 7, line 34, in Claim 11, delete "tipper" and insert -- upper --, therefor.

In column 8, line 6, in Claim 15, after "member" insert -- , --.

Signed and Sealed this

Eighth Day of June, 2010

David J. Kappos
*Director of the United States Patent and Trademark Office*